United States Patent [19]

Won

[11] Patent Number: 4,690,825
[45] Date of Patent: Sep. 1, 1987

[54] METHOD FOR DELIVERING AN ACTIVE INGREDIENT BY CONTROLLED TIME RELEASE UTILIZING A NOVEL DELIVERY VEHICLE WHICH CAN BE PREPARED BY A PROCESS UTILIZING THE ACTIVE INGREDIENT AS A POROGEN

[75] Inventor: Richard Won, Palo Alto, Calif.

[73] Assignee: Advanced Polymer Systems, Inc., Redwood City, Calif.

[21] Appl. No.: 784,382

[22] Filed: Oct. 4, 1985

[51] Int. Cl.$^4$ ................................. C08J 9/28
[52] U.S. Cl. .................................. 424/501; 521/63; 424/502; 514/963; 514/965
[58] Field of Search ................. 424/22; 514/963, 965; 521/63

[56] References Cited

U.S. PATENT DOCUMENTS

| | | | |
|---|---|---|---|
| 3,390,050 | 6/1968 | Speiser | 424/78 |
| 3,516,941 | 6/1970 | Matson | 514/963 |
| 3,720,534 | 3/1973 | Macaulay et al. | 521/63 |
| 3,886,084 | 5/1975 | Vassilades | 264/4 |
| 3,985,298 | 10/1976 | Nichols | 427/214 |
| 3,989,649 | 11/1976 | Kaiho et al. | 521/29 |
| 4,110,529 | 8/1978 | Stoy | 528/491 |
| 4,307,201 | 12/1981 | Won et al. | 521/64 |
| 4,322,311 | 3/1982 | Lim et al. | 424/85 |
| 4,324,683 | 4/1982 | Lim et al. | 424/32 |
| 4,353,809 | 10/1982 | Hoshi et al. | 264/4.7 |
| 4,353,888 | 10/1982 | Sefton | 424/32 |
| 4,353,962 | 10/1982 | Himel et al. | 264/4 |
| 4,391,909 | 7/1983 | Lim | 264/4 |
| 4,396,670 | 8/1983 | Sinclair | 428/321.5 |
| 4,407,957 | 10/1983 | Lim | 435/178 |
| 4,439,488 | 3/1984 | Trimnell et al. | 424/33 |
| 4,444,699 | 4/1984 | Hayford | 264/4.7 |
| 4,464,271 | 8/1984 | Munteanu et al. | 252/8.6 |
| 4,522,953 | 6/1985 | Barby et al. | 521/64 |

FOREIGN PATENT DOCUMENTS

EP61701 10/1982 European Pat. Off.

OTHER PUBLICATIONS

Brunauer, S. Emmet, P.H., & Teller, E., J. Am. Chem. Soc., 60, 309–16 (1938).
Barrett, E.P., Joyner, L. G. & Helenda, P. O., J. Am. Chem. Soc., 73, 373–80 (1951).

Primary Examiner—Ronald W. Griffin
Attorney, Agent, or Firm—Townsend & Townsend

[57] ABSTRACT

Delivery vehicles comprised of a polymeric bead having a network of pores with an active ingredient held within the network are provided for use in a method to provide controlled release of the active ingredient. The network of pores is substantially non-collapsible upon removal of the active ingredient and the delivery vehicles are polymerized by a process in which the active ingredient also comprises the porogen during formation of the network of pores.

80 Claims, 1 Drawing Figure

METHOD FOR DELIVERING AN ACTIVE INGREDIENT BY CONTROLLED TIME RELEASE UTILIZING A NOVEL DELIVERY VEHICLE WHICH CAN BE PREPARED BY A PROCESS UTILIZING THE ACTIVE INGREDIENT AS A POROGEN

BACKGROUND OF THE INVENTION

1. Field of the Invention

The field of the present invention relates generally to delivery vehicles used in a time release method for delivering an active ingredient and processes for producing such vehicles.

2. Description of the Prior Art

There are a wide variety of controlled release products presently being utilized in numerous applications, including pharmaceutical, agricultural and veterinary applications. Generally speaking, an active ingredient is released over time. The active ingredient may be contained in a variety of media, such as coated particles (e.g. sphere, aggregate, multiple coating or pill), solid solutions (e.g. beadlet, film, bandage or cube), compositions (e.g. sphere, tablet, pills or strip), containers (e.g. capsule, breakable ampule or capillary), and combinations (e.g. in a liquid, in a capsule or in a pill).

Microencapsulation is the most common process for preparing a time release delivery vehicle. Generally speaking, microencapsulation utilizes a coating to contain the active ingredient which is then released by rupture or dissolution of the coating. Alternatively, the coating or membrane may be semipermeable or porous to allow the active ingredient to diffuse out of the microencapsule.

U.S. Pat. No. 4,322,311 describes an encapsulation technique for producing semi-permeable or controlled porosity microcapsules. An active ingredient and a monomer in a first solution are emulsified in a hydrophobic solvent. A monomer complementary to the first monomer which is soluble in the hydrophobic solvent is added to the emulsion to initiate interfacial polymerization about the aqueous droplets. During the course of reaction, the affinity of the continuous phase for the first monomer is varied by adding a solvent to the continuous phase to vary its polarity. This promotes diffusion into the continuous phase resulting in a porous membrane. Since the patent describes the use of an amine monomer, some amine monomer may remain encapsulated within the microcapsule.

Another encapsulation technique is described in U.S. Pat. No. 4,444,699 wherein minute capsules are manufactured en masse. The process utilizes polycondensation of melamine with formaldehyde or in situ polymerization of methylol melamine or esterified methylol melamine, or a low molecular weight polymer thereof, in an aqueous vehicle and the reaction is conducted in the presence of polyelectrolyte material and certain salts. However, this process will typically leave some residue of formaldehyde which may pose a health problem.

Other examples of encapsulation techniques include, by way of example only, U.S. Pat. Nos. 4,324,683; 4,353,809; 4,353,888; 4,353,962; 4,391,909; 4,396,670; 4,407,957; 4,439,488; and 4,464,271. The microcapsules produced by these type of processes will typically possess limited mechanical strength and will release all of the active ingredients at once if the membrane is ruptured. The limited mechanical stability can create problems with incorporating the microcapsules into a medium and will also limit the shelf life of these delivery vehicles. In addition, the microcapsules will typically contain reactive groups which can create problems of chemical stability.

Another delivery vehicle for an active ingredient is described in U.S. Pat. No. 3,985,298 which utilizes a process to impregnate an active ingredient into and within a cellulosic polymer-liquid composite material as a part of or all of the liquid phase. The active ingredient is released from the gel matrix which shrinks or collapses as the active ingredient is removed. The gel structure is not mechanically strong and therefore it suffers some of the mechanical problems associated with microspheres.

Accordingly, there exists a need for an economical time-release delivery vehicle with high mechanical strength useful in a controlled-release application.

SUMMARY OF THE INVENTION

The invention relates to a method for delivering an active ingredient by controlled time release. In another aspect of the present invention, a composition of matter and a process for preparing the composition of matter useful in the method of the instant invention are disclosed.

In the instant invention, a delivery vehicle comprised of a polymeric bead having a network of pores with the active ingredient held within the network is utilized to provide a controlled time release of the active ingredient. The active ingredient might be a lubricant, an emollient, a moisturizer, a pigment, an insect or flea repellant, a fragrance, a vitamin, a drug or any other functional ingredient. The delivery vehicle may be incorporated in a medium, such as a gel, a cream, a lotion, an ointment, a liquid or the like, which may then be applied to a surface. The active ingredient may then be released by pressure, diffusion or volatilization. Thus, the delivery vehicle is uniquely suited for use in a wide variety of applications in which it is desirable to release an active ingredient by one or more methods.

A delivery vehicle according to the present invention has increased mechanical stability over a microencapsulated or gel delivery vehicle. The network of pores of a bead according to the present invention will not be subject to osmotic shock which might occur in prior art delivery vehicles. In addition, the increased mechanical stability allows a delivery vehicle to be manufactured, processed and handled under more severe conditions, such as mechanical stirring, which might otherwise rupture or damage prior art gel or microencapsulated delivery vehicles. Thus, a delivery vehicle according to the present invention can easily be incorporated in certain media in which it would prove difficult or more expensive to incorporate delivery vehicles of the prior art.

When a delivery vehicle according to the present invention is polymerized from styrene and divinylbenzene, the delivery vehicle will possess greater chemical stability over previous delivery vehicles because the styrene divinylbenzene polymeric bead will not contain reactive groups and will consist essentially of hydrocarbon backbone with benzene rings. Because the styrene divinylbenzene polymeric bead does not contain reactive groups, the bead will not readily undergo unwanted reactions and the bead will be stable over a very wide pH range, the bead will resist moderate oxidation and reduction, the bead will be stable to higher temperatures, the bead will not be subject to attack by moisture, and the bead will have a longer shelf life. In addition, in contrast to some prior art delivery vehicles, a styrene divinylbenzene polymeric bead of the present invention does not contain any reactive groups or polymeric structure which may cause a problem of toxicity, irritation or the like when applied topographically to skin.

When a delivery vehicle is prepared in accordance with the present invention, the active ingredient is trapped in the network of pores during polymerization of the bead. Thus, in contrast to a process which might adsorb an active ingredient into a preformed matrix, the active ingredient in a delivery vehicle of the present invention should have a substantially uniform concentration throughout the network of pores. This uniformity helps to create a more controlled time release of the active ingredient from the network of pores over a given period of time. Further, the delivery vehicle of the instant invention is capable of providing a sustained release over a period of time as compared to a total release when the membrane of a microencapsulated delivery vehicle is broken.

Another advantage of a delivery vehicle prepared in accordance with the present invention is the substantial absence of unreacted monomer. Thus, in a microencapsulation delivery vehicle it may be difficult to remove unreacted monomer because it might become encapsulated along with the active ingredient inside of the membrane. This problem is especially accute in some prior art delivery vehicles which utilize urea-formaldehyde microencapsules which can create potential health problems.

Accordingly, it is a primary object of the present invention to provide a delivery vehicle for delivering an active ingredient by controlled time release over a period of time.

This and further objects and advantages of the present invention will become apparent to one of ordinary skill in the art in connection with the detailed description of the preferred embodiments set forth below.

DETAILED DESCRIPTION OF THE PREFERRED EMBODIMENT

Figure 1:
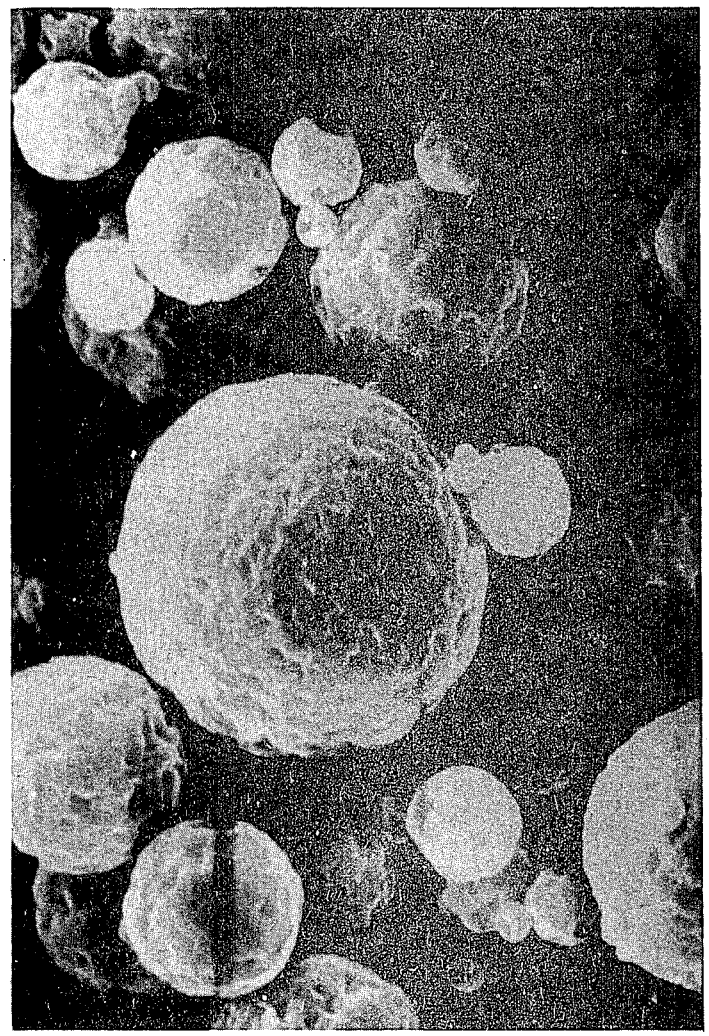
FIG. 1 is a photomicrograph of a plurality of delivery vehicles produced according to the present invention.

In accordance with the present invention, an active ingredient is released from a network of pores by controlled time release. The active ingredient can be defined as a functional ingredient or an ingredient which is released from the network of pores to perform some function. Thus, for example, when the active ingredient is a drug used in a dermatologic medication, the active ingredient might comprise anti-infectives (such as antibiotics, fungicides, scabicides pediculicides or miscellaneous anti-infectives such as iodine), anti-inflammatory agents, antipruritics, astringents, anti-hidrotics, keratolytic agents and caustics, keratoplastic agents, rubefacients, sunscreens, pigmentation agents, emollients, demukents, protectants and detergents. In addition to use as a dermatologic medication, the active ingredient might be used in a variety of other applications such as beauty aids, including cosmetic and toiletry applications, and the active ingredient may be incorporated in a medium such as a gel, a cream, a lotion, an ointment, a liquid or the like. The delivery vehicle containing the active ingredient might be incorporated into cosmetic preparations such as hand creams, acne products, deodorants, antiperspirants, baby powders, foot powders, body powders, lip ices, lip sticks, baby creams and lotions, mouthwashes, dentifrices, medicated facial creams and lotions, shampoos, shaving creams, pre- and after-shave lotions, depilatories and hairgrooming preparations. The active ingredient may be comprised of a carrier and an agent wherein the carrier is used to deliver the agent and the agent is the functional ingredient. Thus, for example, the agent might be a solid suspended in an agent. Accordingly, the term active ingredient is meant to encompass a whole host of possible compositions or substances so long as the active ingredient is held within the network of pores of a porous bead according to the present invention.

A delivery vehicle according to the present invention can be prepared by polymerizing one or more polymers by a free radical suspension polymerization process. A monomer or pair of comonomers is dissolved in an inert porogen, which is also the active ingredient, to form a solution which is suspended in a phase or solvent incompatible with the solution.

An example of a phase or solvent might be water with stabilizing additives. After the solution is suspended in the phase, the solution and phase are agitated to form a plurality of droplets of solution suspended in the phase. After the formation of the plurality of droplets, the monomer or monomers in the plurality of droplets are activated to initiate a polymerization reaction in which a monomer is cross-linked or two or more monomers are polymerized to form porous beads having a network of pores with the porogen held within the network of pores. The activation may be triggered by an initiator which is soluble in the monomer solution. Alternatively, activation may be triggered by an energy source such as radiation. The inert porogen will serve as an internal diluent during polymerization to introduce the desired sponge-like macroporous structure or network of pores into the finished delivery vehicle. The inert porogen should not react with the monomer present during polymerization or inhibit the polymerization. The bead of the delivery vehicle may or may not swell in the inert porogen. After the formation of the porous beads, the beads are separated from the phase and subjected to one or more purification steps, such as washing, to remove any unreacted monomer or impurity from the beads. The purification of the beads should not be designed to remove the porogen from the network of pores in each of the beads. After purification, the beads may be dried to obtain a powder-like substance comprised of the beads which have retained the porogen within the network of pores to serve as an active ingredient when the beads are used as a time-release delivery vehicle.

The process of the present invention can be designed so as to control porosity and the particle diameter of the beads which may be considered substantially spherical. Under identical polymerization conditions, the porosity can be increased by increasing the calculated or theoretical cross-linking density or by increasing the porogen concentration in the solution. An increase in porosity will increase the surface area of the bead and hence the weight percent of the porogen which can be held within the bead. To decrease the particle diameter under identical polymerization conditions, the agitation or the concentration of dispersion agents in the phase should be increased. By controlling the porosity and the particle diameter of the bead, a delivery vehicle suitable for use in the method of the present invention can be obtained. Generally speaking, it has been found that it is preferable for the bead to have a diameter from about 10 microns to about 100 microns, and have a calculated cross-linking in excess of about 10%. The active ingredient should comprise between approximately 5% to approximately 60% of the total weight of the composition or delivery vehicle comprising the polymeric bead and the active ingredient.

To distinguish whether a composition possesses sufficient mechanical strength to be used as a delivery vehicle for providing controlled time-release of the active ingredient, the composition can be subjected to a wetting test. If the composition has a calculated cross-linking density and an active ingredient concentration such that substantially all of the active ingredient will be released from the network of pores when the bead is placed in a solvent, in which the active ingredient is soluble, for a sufficient length of time to wet the bead, then the composition can be used in the method of the present invention.

A wetting test can be performed by weighing a dry sample of material to be tested containing an original amount of active ingredient. The dry sample is then mixed with a solvent in which the active ingredient is soluble to form a wet sample. The wet sample is then agitated for a sufficient length of time to wet the bead if the dry sample is comprised of a delivery vehicle according to the present invention. The amount of active ingredient released into the solvent is then determined. The amount of active ingredient released into the solvent will be substantially the same as the original amount of active ingredient if the dry sample consisted essentially of the delivery vehicle whereas the released amount will be substantially less than the original amount if the dry sample contained a substantial amount of a gel product or a microencapsulated product.

The process of the present invention can be conducted without using expensive and environmentally toxic solvents such as chloroform or other chlorinated solvents which are often used in interfacial polymerization. Further, since it is desired to leave the porogen held within the network of pores, there is no need for an additional washing step in which the porogen must be dissolved to be removed from the network of pores. Accordingly, the process of the present invention can be very economical with a minimal exposure of possible environmental pollution when a suitable activator and phase or solvent are selected.

To utilize a delivery vehicle in accordance with the method of the present invention, the delivery vehicle is mixed with a medium to form a mixture which is applied to a surface. The active ingredient is then released from the network of pores by a force or energy. The controlled time release might occur through diffusion or volatization, both of which are attributable to changes in kinetic energy. Alternatively, the active ingredient may be released by a force such as pressure. Pressure release may by gradual and continuous. Pressure release may also be triggered by intermittent pressure which may vary the concentration of active ingredient released from the network of pores.

A delivery vehicle of the present invention is mechanically strong because of the polymeric structure of the bead and the degree of cross-linking or copolymerization. It is believed that the bead can be conceptualized as a rigid sponge, i.e., a structural network formed by three dimensional cross-linking or copolymerization which leaves random spaces or holes which collectively form the network of pores. The polymer structure or bead physically holds the active ingredient in the network of pores because the active ingredient diffuses into the polymeric structural network being formed during polymerization of the bead, and is then held or trapped until an external force or energy releases the porogen from the network of pores in the polymerized bead. However, unlike a gel in which the polymeric structural network collapses when the material held within said network is removed or released, a delivery vehicle according to the present invention must possess a certain minimum degree of calculated cross-linking density for a given active ingredient concentration so as to give the entire structure or bead sufficient strength to prevent substantial shrinking or collapse of the bead when porogen is removed from the network of pores.

The invention will be further illustrated in the example that follows wherein the delivery vehicle is copolymerized from styrene and divinylbenzene which is an especially preferred comonomer pair because of the chemical stability of styrene divinylbenzene. As would be apparent to one skilled in the art, the term "divinylbenzene" as used in this description, as well as in the appended claims, is meant to include pure divinylbenzene as well as commercial divinylbenzene which is really a mixture of divinylbenzene and ethylvinylbenzene. Other preferred comonomer pairs are vinyl stearate and divinylbenzene, and methylmethacrylate and ethylene glycol dimethylmethacrylate. In the following example the active ingredient and porogen is mineral oil which is an especially preferred wetting agent in many beauty aids. Other similar wetting agents might include vegetable oils or sunflower oil.

EXAMPLE I

A 2000 ml four - necked reaction flask equipped with a stirrer, condenser, thermometer, and nitrogen inlet was evacuated and charged with nitrogen. 900 ml deionized water, 7.2 grams of gum arabic and 7.2 grams of a lignosulfonate available from the American Can Co. under the trademark Marasperse N-22, were charged into the reaction flask. The mixture was stirred and heated in an oil bath at about 60 degrees Celsius until the dispersants dissolved to form a phase. To this mixture was added a freshly prepared solution of 90.8 grams of styrene (99.8% purity), 45.2 grams commercial divinylbenzene (55.6% divinylbenzene, 42.3% ethylvinylbenzene), 2.5 grams benzoyl peroxide (70% active ingredient and 30% water), and 146.0 grams of mineral oil. The initiator benzoyl peroxide was dissolved in monomer before mineral oil is added because mineral oil does not readily dissolve benzoyl peroxide unless benzoyl peroxide is dissolved in a monomer. The phase and solution were agitated by a mechanical stirrer whose stirring rate was adjusted to obtain a plurality of droplets having a droplet diameter in the range of 5 to 80 microns. The gum arabic and lignosulfonate serve to stabilize the plurality of droplets. The reaction mixture was then heated to about 95 degrees Celsius and and maintained at that temperature for about 18 to 20 hours at the adjusted stirring rate to form porous beads of styrene divinylbenzene having a network of pores with mineral oil held within the network of pores. The mixture was then cooled, the porous polymeric beads were removed from the reaction flask by filtration, washed initially three times with one liter of water to remove gum arabic and lignosulfonate, followed by three washes of 1 liter of methanol to remove residual or unreacted monomer. The purified product was then dried to remove methanol and the resulting polymeric delivery vehicles were white and opaque indicating their macroporosity.

The calculated or theoretical cross-linking density of the purified beads is 18.5%. This density is calculated by multiplying the weight of divinylbenzene (45.2 g) by the purity of the divinylbenzene (0.556) to get the actual weight of pure divinylbenzene which is then divided by the total weight of monomer (45.2 g + 90.8 g).

The surface area of a sample of the purified beads was determined by the B.E.T. method to be 7.25 meters$^2$/gram while the pore volume was determined by nitrogen adsorption isotherm to be 0.1028 ml./gram. The B.E.T. method is described in detail in Brunauer, S. Emmet, P. H., and Teller, E., J.Am.Chem.Soc., 60, 309–16 (1938). The nitrogen adsorption isotherm method is described in detail in Barrett, E. P., Joyner, L. G. and Helenda, P. P., J.Am.Chem.Soc., 73, 373–80 (1951). The sample used in these methods was prepared by dissolving the mineral oil in ethylacetate to remove the mineral oil from the network of pores.

A sample of the purified delivery vehicles was also subjected to a wetting test. 2.0 grams of the purified beads was accurately weighed and then placed into a 250 ml. glass stoppered flask. 100.0 ml. of hexane was added to the flask by a pipet. A stopper was then placed in the flask which was clamped to a Burrel brand mechanical shaker set at its highest speed (10) for 5±1 minutes. The liquid was immediately filtered through Whatman paper #54. A 20 ml. sample was removed by pipet and placed into a tared glass container which was placed on a steam bath or under a heat lamp until the hexane was evaporated. The container was then placed in an oven maintained at a temperature of 105° C. for 30 minutes. The container was then cooled and weighed. The percentage of free oil was calculated as follows:

$$\% \text{ Free Oil} = \frac{\text{wt. of residue}}{\text{wt. of sample}} \times 100 \times 5$$

The % free oil was 50% of the total weight of the sample. Since the sample or delivery vehicle was comprised of approximately 50% by weight bead and approximately 50% by weight mineral oil, substantially all of the active ingredient was released from the network of pores of the beads into the solvent.

The particle size of the beads was determined by an optical microscope to be 40 microns or less with an average particle size diameter within the range from about 10 microns to about 30 microns.

Another dry sample of the purified delivery vehicles was placed into a capped glass bottle and stored in a shelf with a glass door for approximately one year. The bottle was airtight. After approximately one year the bottle was opened and no change in visual characteristics of the sample was observed. A wetting test was performed on a sample obtained from the bottle. Once again, substantially all of the mineral oil was released from the network of pores of the beads. A photomicrograph picture was then taken of a sample obtained from the bottle. The picture was taken on an electron microscope with a magnification of 6000×. The picture is reproduced in FIG. 1.

EXAMPLES II–IV

These examples were carried out under identical reaction conditions as those of Example I except for the weight of the monomers and mineral oil utilized in the reaction. These values are set forth in Table I.

TABLE I

| Example | Styrene | DVB | Mineral Oil |
|---------|---------|------|-------------|
| II      | 41.0    | 9.0  | 55.0        |
| III     | 61.4    | 73.6 | 146.0       |
| IV      | 13.6    | 36.4 | 55.0        |

Samples obtained from Examples II–IV had an average particle size diameter within the range of from about 10 microns to about 50 microns. Samples from these Examples were subjected to the wetting test described in Example 1 and substantially all of the mineral oil was released from the network of pores of the beads of each of the Examples. The calculated cross-linking density, surface area and pore volume of each of Examples II through IV were obtained according to the procedures described in Example I and the data is set forth in Table II.

TABLE II

| Example | Cross-linking, D.V.B. % | Surface Area M$^2$/gram | Pore Volume ml/g |
|---------|-------------------------|-------------------------|------------------|
| II      | 10.0                    | 3.65                    | 0.6130           |
| III     | 30.0                    | 14.97                   | 0.1010           |
| IV      | 40.0                    | 249.0                   | 0.7585           |

EXAMPLE V

Once again, this example was carried out under identical reaction conditions as those of Example I except for the weight of the monomers and mineral oil utilized in the reaction. The example used 42.7 grams of styrene, 7.3 grams of divinylbenzene (DVB) and 55.0 grams of mineral oil. The theoretical cross-linking density was 8.0 and the surface area was 1.93 meters$^2$/gram while the pore volume was 0.0284 ml/gram. The average particle size diameter was within the range of from about 10 microns to about 50 microns. However, when a sample of the composition was subjected to the wetting test described in Example I, the percentage of free oil was found to be 10% indicating that the composition is a gel bead which is not macroporous and would not be acceptable for use in the method of controlled time-release of the instant invention.

Having fully described the present invention, it will be apparent from the above description and drawing that various modifications in the specific compositions, procedures, methods and processes may be made within the scope of the invention. Therefore, the invention is not intended to be limited to the particular compositions, processes or methods except as may be required by the lawful scope of the following claims.

What is claimed is:

1. A composition of matter useful as a time-release delivery vehicle for delivering an active ingredient by controlled time release, comprising a porous polymeric bead having a network of pores with the active ingredient held within the network of pores, said network of pores being substantially non-collapsible upon removal of the active ingredient.

2. A composition of matter as recited in claim 1 wherein the bead is copolymerized from a comonomer pair selected from the groups consisting of vinyl stearate and divinylbenzene, and methylmethacrylate and ethylene glycol dimethylmethacrylate.

3. A composition of matter as recited in claim 1 wherein the bead has a diameter from about 10 microns to about 100 microns.

4. A composition of matter as recited in claim 1 wherein the active ingredient is a porogen.

5. A composition of matter as recited in claim 4 wherein the porogen is comprised of mineral oil.

6. A composition of matter as recited in claim 1 wherein the bead has a calculated cross-linking density in excess of about 10%.

7. A composition of matter as recited in claim 1 wherein the active ingredient comprises between approximately 5% to approximately 60% of the total weight of the composition.

8. A process for preparing a time-release delivery vehicle useful for delivering an active ingredient by controlled release, comprising the steps of:
dissolving at least one monomer in an inert porogen to form a solution;
suspending the solution in a phase incompatible with the solution;
agitating the solution and the phase to form a plurality of droplets of the solution suspended in the phase;
activating at least one monomer in the plurality of droplets to polymerize at least one monomer and form a porous bead having a network of pores with the porogen held within the network of pores, said network of pores being substantially non-collapsible upon removal of the porogen;
separating the porous polymeric bead from the phase;
removing any impurity from the porous polymeric bead; and
retaining the porogen within the network of pores as the active ingredient to form the delivery vehicle.

9. A process as recited in claim 8 wherein one monomer is cross-linked to form the porous bead.

10. A process as recited in claim 8 wherein a comonomer pair is copolymerized to form the bead, said comonomer pair being selected from the groups consisting of vinyl stearate and divinylbenzene, and methylmethacrylate and ethylene glycol dimethylmethacrylate.

11. A process as recited in claim 8 wherein the porogen is mineral oil.

12. A process as recited in claim 8 wherein the polymeric bead has a diameter from about 10 microns to about 100 microns.

13. A process as recited in claim 8 wherein the polymeric bead has a calculated cross-linking density in excess of about 10%.

14. A process as recited in claim 10 wherein the comonomer pair is styrene and divinylbenzene which are activated by an initiator which is soluble in styrene and divinylbenzene.

15. A process as recited in claim 10 wherein the comonomer pair is activated by an initiator which is soluble in the comonomer pair.

16. A method for delivering an active ingredient by controlled time release, comprising the steps of:
mixing a delivery vehicle with a medium to form a mixture, said delivery vehicle comprising a porous polymeric bead having a network of pores with the active ingredient held within the network of pores said network of pores being substantially non-collapsible upon removal of the active ingredient;
applying the mixture to a surface; and
releasing the active ingredient from the network of pores.

17. A method as recited in claim 16 wherein the delivery vehicle has a diameter from about 10 microns to about 100 microns.

18. A method as recited in claim 16 wherein the active ingredient is a porogen.

19. A method as recited in claim 18 wherein the porogen is comprised of mineral oil.

20. A method as recited in claim 16 wherein the delivery vehicle has a calculated cross-linking density in excess of about 10%.

21. A method as recited in claim 16 wherein the active ingredient comprises between approximately 5% to approximately 60% of the total weight of the delivery vehicle.

22. A method as recited in claim 16 wherein the active ingredient is released by pressure.

23. A method as recited in claim 16 wherein the active ingredient is released by diffusion.

24. A method as recited in claim 16 wherein the active ingredient is released by volatization.

25. A method as recited in claim 22 wherein the active ingredient is gradually and continuously released from the network of the pores.

26. A method as recited in claim 16 wherein the active ingredient is comprised of a carrier and an agent.

27. A method as recited in claim 16 wherein the polymeric bead is copolymerized from a comonomer pair selected from the groups consisting of vinyl stearate and divinylbenzene, and methylmethacrylate and ethylene glycol dimethylmethacrylate.

28. A composition of matter useful as a time-release delivery vehicle for delivering an active ingredient by controlled time release, comprising a porous polymeric bead of styrene divinylbenzene having a network of pores with the active ingredient held within the network of pores, said network of pores being substantially non-collapsible upon removal of the active ingredient.

29. A composition of matter as recited in claim 28 wherein the bead has a diameter from about 10 microns to about 100 microns.

30. A composition of matter as recited in claim 28 wherein the active ingredient is a porogen.

31. A composition of matter as recited in claim 30 wherein the porogen is comprised of mineral oil.

32. A composition of matter as recited in claim 28 wherein the bead has a calculated cross-linking density in excess of about 10%.

33. A composition of matter as recited in claim 28 wherein the active ingredient comprises between approximately 5% to approximately 60% of the total weight of the composition.

34. A process for preparing a time-release delivery vehicle useful for delivering an active ingredient by controlled time-release, comprising the steps of:
dissolving styrene and divinylbenzene in an inert porogen to form a solution;
suspending the solution in a phase incompatible with the solution;
agitating a plurality of the solution and the phase to form droplets of the solution suspended in the phase;
activating styrene and divinylbenzene in the plurality of droplets to copolymerize the styrene and divinylbenzene and form at least one porous polymeric bead of styrene divinylbenzene having a network of pores with the porogen held within the network of pores, said network of pores being substantially non-collapsible upon removal of the porogen;

separating the porous polymeric bead from the phase;

removing any impurity from the porous polymeric bead; and retaining the porogen within the network of pores as the active ingredient to form the time-release delivery vehicle.

35. A process as recited in claim 34 wherein the porogen is mineral oil.

36. A process as recited in claim 34 wherein the polymeric bead has a diameter from about 10 microns to about 100 microns.

37. A process as recited in claim 34 wherein the polymeric bead has a calculated cross-linking density in excess of about 10%.

38. A process as recited in claim 34 wherein the active ingredient comprises between approximately 5% to approximately 60% of the total weight of the delivery vehicle.

39. A process as recited in claim 34 wherein the styrene and divinylbenzene are activated by an initiator which is soluble in styrene and divinylbenzene.

40. A method for delivering an active ingredient by controlled time release; comprising the steps of:

mixing a delivery vehicle with a medium to form a mixture, said delivery vehicle comprising a porous polymeric bead of styrene divinylbenzene having a network of pores with the active ingredient held within the network of pores, said network of pores being substantially non-collapsible upon removal of the active ingredient;

applying the mixture to a surface; and releasing the active ingredient from the network of pores.

41. A method as recited in claim 40 wherein the delivery vehicle has a diameter from about 10 microns to about 100 microns.

42. A method as recited in claim 40 wherein the active ingredient is a porogen.

43. A method as recited in claim 42 wherein the porogen is comprised of mineral oil.

44. A method as recited in claim 40 wherein the delivery vehicle has a calculated cross-linking density in excess of about 10%.

45. A method as recited in claim 40 wherein the active ingredient comprises between approximately 5% to approximately 60% of the total weight of the delivery vehicle.

46. A method as recited in claim 40 wherein the active ingredient is released by pressure.

47. A method as recited in claim 40 wherein the active ingredient is released by diffusion.

48. A method as recited in claim 40 wherein the active ingredient is released by volatization.

49. A method as recited in claim 46 wherein the active ingredient is gradually and continuously released from the network of the pores.

50. A method as recited in claim 40 wherein the active ingredient is comprised of a carrier and an agent.

51. A composition of matter useful as a time-release delivery vehicle for delivering an active ingredient by controlled time release, comprising a porous polymeric bead having a network of pores with the active ingredient held within the network of pores, said composition having a calculated cross-linking density and an active ingredient concentration such that substantially all of the active ingredient will be released from the network of pores when the bead is placed in a solvent in which the active ingredient is soluble for a sufficient length of time to wet the bead.

52. A composition of matter as recited in claim 51 wherein substantially all of the active ingredient will be released from the network of pores within about 5 minutes with moderate agitation of the solvent and the composition.

53. A composition of matter as recited in claim 51 wherein the bead is polymerized from a comonomer pair selected from the groups consisting of styrene and divinylbenzene, vinyl stearate and divinylbenzene, and methylmethacrylate and ethylene glycol dimethacrylate.

54. A composition of matter as recited in claim 53 wherein the active ingredient is mineral oil.

55. A composition of matter as recited in claim 51 wherein the active ingredient is a porogen.

56. A composition of matter as recited in claim 55 wherein the active ingredient is mineral oil.

57. A composition of matter as recited in claim 51 wherein the bead has a diameter from about 10 microns to about 100 microns.

58. A composition of matter as recited in claim 51 wherein the bead has a calculated cross-linking density in excess of about 10%.

59. A composition of matter as recited in claim 51 wherein the active ingredient comprises between approximately 5% to approximately 60% of the total weight of the composition.

60. A process for preparing a time-release delivery vehicle useful for delivering an active ingredient by controlled time-release, comprising the steps of:

dissolving at least one monomer in an inert porogen to form a solution;

suspending the solution in a phase incompatible with the solution;

agitating the solution and the phase to form a plurality of droplets of the solution suspended in the phase;

activating at least one monomer in the plurality of droplets to polymerize at least one monomer and form a porous bead having a network of pores with the porogen held within the network of pores;

separating the porous polymeric bead from the phase;

removing any impurity from the porous polymeric bead; and retaining the porogen within the network of pores as the active ingredient to form the delivery vehicle, said delivery vehicle having a calculated cross-linking density and an active ingredient concentration such that substantially all of the active ingredient will be released from the network of pores when the bead is placed in a solvent in which the active ingredient is soluble for a sufficient length of time to wet the bead.

61. A process as recited in claim 60 wherein a comonomer pair is polymerized to form the bead, said comonomer pair being selected from the groups consisting of styrene and divinylbenzene, vinyl stearate and divinylbenzene, and methylmethacrylate and ethylene glycol dimethymethacrylate.

62. A process as recited in claim 61 wherein the comonomer pair is activated by an initiator which is soluble in the comonomer itself.

63. A process as recited in claim 61 wherein the porogen is mineral oil.

64. A process as recited in claim 60 wherein a comonomer pair is copolymerized to form the bead, said comonomer pair being selected from the groups consisting of vinyl stearate and divinylbenzene, and methylmethacrylate and ethylene glycol dimethymethacrylate.

65. A process as recited in claim 60 wherein the polymeric bead has a diameter from about 10 microns to about 100 microns.

66. A process as recited in claim 60 wherein the polymeric bead has a calculated cross-linking density in excess of about 10%.

67. A process as recited in claim 60 wherein the active ingredient comprises between approximately 5% to approximately 60% of the total weight of the delivery vehicle.

68. A method for delivering an active ingredient by controlled time release, comprising the steps of:

mixing a delivery vehicle with a medium to form a mixture, said delivery vehicle comprising a porous polymeric bead having a network of pores with the active ingredient held within the network of pores, said delivery vehicle having a calculated cross-linking density and an active ingredient concentration such that substantially all of the active ingredient will be released from the network of pores when the bead is placed in a solvent of pores in which the active ingredient is soluble for a sufficient length of time to wet the bead;

applying the mixture to a surface; and releasing the active ingredient from the network of pores.

69. A method as recited in claim 68 wherein the polymeric bead is copolymerized from a comonomer pair selected from the groups consisting of styrene and divinylbenzene, vinyl stearate and divinylbenzene, and methylmethacrylate and ethylene glycol dimethylmethacrylate.

70. A method as recited in claim 69 wherein the active ingredient is comprised of mineral oil.

71. A method as recited in claim 68 wherein the delivery vehicle has a diameter from about 10 microns to about 100 microns.

72. A method as recited in claim 68 wherein the active ingredient is a porogen.

73. A method as recited in claim 72 wherein the porogen is comprised of mineral oil.

74. A method as recited in claim 68 wherein the delivery vehicle has a calculated cross-linking density in excess of about 10%.

75. A method as recited in claim 68 wherein the active ingredient comprises between approximately 5% to approximately 60% of the total weight of the delivery vehicle.

76. A method as recited in claim 68 wherein the active ingredient is released by pressure.

77. A method as recited in claim 76 wherein the active ingredient is gradually and continuously released from the network of the pores.

78. A method as recited in claim 68 wherein the active ingredient is released by diffusion.

79. A method as recited in claim 68 wherein the active ingredient is released by volatization.

80. A method as recited in claim 68 wherein the active ingredient is comprised of a carrier and an agent.

* * * * *